United States Patent
Huber et al.

(10) Patent No.: US 9,958,467 B2
(45) Date of Patent: May 1, 2018

(54) METHOD FOR SUPPLEMENTING A SAMPLE WITH SPECIFIC INFORMATION AND SAMPLE TUBE SYSTEM

(71) Applicant: numares AG, Regensburg (DE)

(72) Inventors: Fritz Huber, Regensburg (DE); Volker Pfahlert, Kandern (DE); Markus Fuhrmann, Maxhuette-Haidhof (DE); Renate Kirchhöfer, Regensburg (DE)

(73) Assignee: numares AG, Regensburg (DE)

( * ) Notice: Subject to any disclaimer, the term of this patent is extended or adjusted under 35 U.S.C. 154(b) by 16 days.

(21) Appl. No.: 14/651,258

(22) PCT Filed: Dec. 11, 2013

(86) PCT No.: PCT/EP2013/076236
§ 371 (c)(1),
(2) Date: Jun. 11, 2015

(87) PCT Pub. No.: WO2014/090879
PCT Pub. Date: Jun. 19, 2014

(65) Prior Publication Data
US 2015/0331002 A1  Nov. 19, 2015

Related U.S. Application Data

(60) Provisional application No. 61/737,248, filed on Dec. 14, 2012.

(30) Foreign Application Priority Data

Dec. 14, 2012  (EP) ..................................... 12197256

(51) Int. Cl.
*G01N 35/00* (2006.01)
*G01N 33/50* (2006.01)

(52) U.S. Cl.
CPC ....... *G01N 35/00732* (2013.01); *G01N 33/50* (2013.01); *G01N 2035/00831* (2013.01); *Y10T 436/13* (2015.01)

(58) Field of Classification Search
CPC ............................................ G01N 2035/00831
See application file for complete search history.

(56) References Cited

U.S. PATENT DOCUMENTS 5,387,526 A * 2/1995 Garner ..................... B01L 3/508
356/244
5,591,403 A * 1/1997 Gavin ................. G01N 33/4905
422/73

(Continued)

FOREIGN PATENT DOCUMENTS

EP  2182367 A2  5/2010
EP  2392928 A1  12/2011

(Continued)

OTHER PUBLICATIONS

Finkel, Nancy H. et al. "Barcoding the microworld." Analytical Chemistry (2004) 76 352a-359a.*

*Primary Examiner* — Christopher Adam Hixson
(74) *Attorney, Agent, or Firm* — The Webb Law Firm

(57) ABSTRACT

Provided is a method for supplementing a sample with specific information. This method includes the following steps: intrinsically marking a sample by adding a chemical marker having a defined composition to the sample; storing data reflecting the composition of the chemical marker and information assigned to the chemical marker, wherein this marker-assigned information is not related to the composition of the chemical marker itself; analyzing the sample with an analysis method, wherein the analysis method is suited to detect the composition of the chemical marker, to obtain a marker-related result; comparing the marker-related result with the stored data; and assigning the marker-assigned (Continued)

stored information to the sample based on the preceding comparison.

11 Claims, 1 Drawing Sheet

(56) References Cited

U.S. PATENT DOCUMENTS

| | | | | |
|---|---|---|---|---|
| 5,677,187 | A | * 10/1997 | Anderson, II | C06B 23/008 436/106 |
| 2002/0125313 | A1 | * 9/2002 | Broff | G06Q 30/02 235/383 |
| 2004/0191765 | A1 | 9/2004 | Mozdy et al. | |
| 2006/0213964 | A1 | * 9/2006 | Excoffier | B01L 3/5457 235/375 |
| 2006/0223078 | A1 | 10/2006 | Changming et al. | |
| 2009/0088336 | A1 | 4/2009 | Burd et al. | |

FOREIGN PATENT DOCUMENTS

| | | |
|---|---|---|
| WO | 0051058 A1 | 8/2000 |
| WO | 2012094625 A2 | 7/2012 |

* cited by examiner

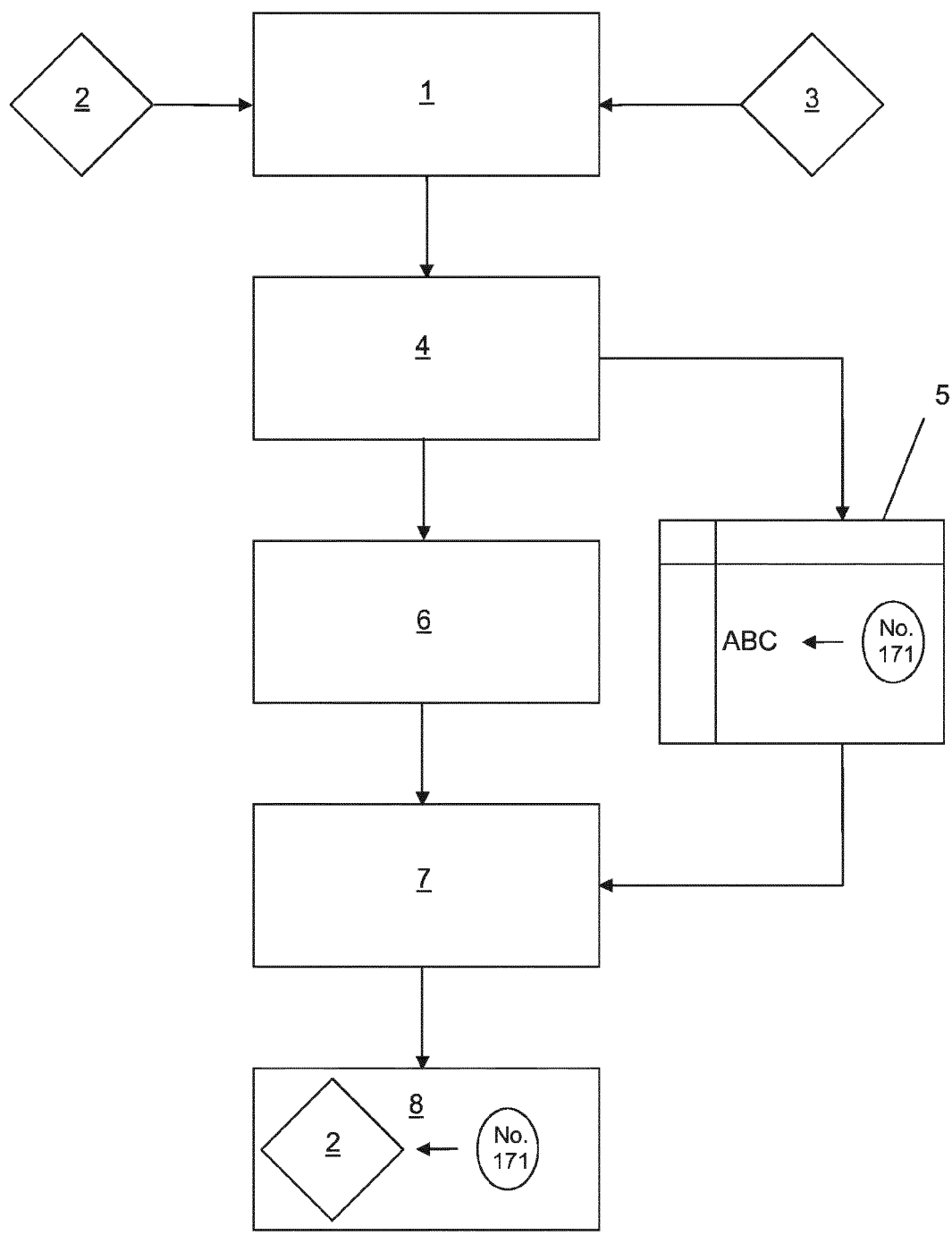

METHOD FOR SUPPLEMENTING A SAMPLE WITH SPECIFIC INFORMATION AND SAMPLE TUBE SYSTEM

CROSS-REFERENCE TO RELATED APPLICATIONS

This application is the United States national phase of International Application No. PCT/EP2013/076236 filed Dec. 11, 2013, and claims priority to European Patent Application No. 12197256.6 filed Dec. 14, 2012, and U.S. Provisional Application No. 61/737,248, filed Dec. 14, 2012, the disclosures of which are hereby incorporated in their entirety by reference.

BACKGROUND OF THE INVENTION

Field of the Invention

The invention relates to a method for supplementing a sample with specific information according to a use for a compound chosen from a specific group and a sample tube system.

Description of Related Art

When biological or other samples are processed, stored or analyzed, it is important that each sample is marked to guarantee, e.g., the identity of the sample or the correct assignment of analysis results to a specific sample. It is known from prior art to mark sample tubes with according information, e.g., provided on a label or a tag. It is also known from prior art to provide the necessary information for sample identification as clear information or in form of a code. For example, barcode labels applied to sample tubes are regularly used to identify samples present within the sample tube.

However, such labels or tags can be detached from a sample tube by accident so that sample identification would be no longer possible. If the sample information is written onto a sample tube, such written information can be blurred due to the interaction with according solvents. In addition, such information can be made illegible due to mechanic interactions or exposure of the sample tubes to substances or radiation acting aggressively on the written information.

US 2009/0088336 A1 describes devices, systems, and methods for automatic quantification of a pharmacological parameter of a patient as well as automatic comparison of the parameter with a patient's medical records. Coupling real-time analyte monitoring with an external device which can store data as well as perform any type of data processing or algorithm provides a device that can assist with typical patient care which can include comparing current patient data with past patient data. That US patent application is mainly directed to a system that includes addressable assay units and addressable reagent units, wherein the presence of an analyte is detected and specific chemical reactions are enabled in response to this detection. That US patent application does, however, not relate to an intrinsic individual information storage like the instantly claimed invention.

WO 2012/094625 A2 relates to a cartridge for an immunoassay test and thus—like U.S. 2009/0088336 A1—to a spatial compartmentalization of reaction spaces or units. It describes how individual samples are processed by different reaction or rinsing solutions. It does, however, not describe that any sample could be individually, reliably and uniquely marked by an intrinsic chemical marker. It does neither describe that individual compartments of the cartridge could be individually marked by a chemical marker.

SUMMARY OF THE INVENTION

It is an object of the present invention to provide a method for adding information to a sample being more reliable than the methods known from prior art.

This object is achieved by a method for supplementing a sample with specific information having the features as described herein. This method comprises the following steps explained below.

Firstly, a sample is intrinsically marked by adding a chemical marker to the sample. The chemical marker has a defined composition. The composition of the chemical marker and information assigned to this specific chemical marker is stored in appropriate data. Thereby, the information that is assigned to the marker is not related to the composition of the chemical marker itself. Rather, this information is "external" information which can be arbitrarily chosen from any desired information.

Afterwards, the sample is analyzed with an analysis method. Thereby, the analysis method is suited to detect the composition of the chemical marker. "Composition" preferably relates to qualitative and quantitative data. A marker-related result is obtained by this analyzing step. In an embodiment, the analysis of the sample does not only provide a marker-related result, but in fact is suited to get a substantial result with respect to the sample itself, wherein the marker-related result is only a co-result. Alternatively, it is also possible to analyze the sample with a first analyzing method to obtain a sample-related result and to analyze the sample with a second analysis method to obtain a marker-related result.

Afterwards, the marker-related result is compared with the stored data. In doing so, it is possible to assign the marker-assigned stored information to the sample that has just been analyzed. Thus, the analysis of the sample preferably provides data on the sample itself and on the specific information that has been added to the sample.

Expressed in other words, the claimed method relates to an intrinsic barcode which is composed of a chemical marker that is added to the sample. This intrinsic barcode becomes an integral part of the sample so that no loss of a label, tag or otherwise presented data can occur. Such an intrinsic barcode strongly enhances the reliability of analysis methods since it allows the unique identification of each analyzed sample.

In doing so, the sample serves as programmable data carrier. The information to be stored within the sample is encoded by the specific composition of the added chemical marker. Thus, adding the chemical marker to the sample has an effect like writing information onto a CD. Specifically, since in most cases it will not be possible to remove the chemical marker anymore from the sample, the information is safely kept together with the sample.

As indicated above, the specific information which is added in form of a specific marker to the sample can generally be any desired information. In an embodiment, the specific information is information for a unique identification of the sample. For example, unique numbers can be assigned to different markers. Once the marker is identified, the number of the according sample can be decoded. Alphanumeric information is also very well suited for unique identification of the sample.

In another embodiment, the specific information is information on a user of the analysis method. This can help tracking a sample within a laboratory and might be helpful when applying methods of good laboratory practice (GLP).

In another embodiment, the specific information is information on a manufacturer of an ingredient of the sample. Such information might be helpful in detecting possible contamination sources or in detecting sources that might be the ground for difficulties in the applied analysis method.

In another embodiment, the specific information is information on the origin of the sample. Such information might also be helpful in identifying a sample and might be used as indicator for a parameter set to be chosen within the applied analysis method.

In another embodiment, the specific information is information on an expiration date of an ingredient of the sample. It is, e.g., possible to block a sample-related analysis result if the expiration date of some of the ingredients of the sample has already expired. In such a case, the obtained sample-related data might not be reliable. If, however, the date of the analysis lies before the expiration date of any or all of the ingredients of the analyzed sample, such information enhances the quality of the whole analysis. In a similar manner, the specific information can be, in another embodiment, information on the term of a license to perform an analysis method. If the license term has expired, no analysis results will be displayed or stored anymore.

In another embodiment, the specific information is information on the time point at which the sample was obtained or manipulated. Such information can again be used to better track the according sample and to assure that the sample itself is sufficiently fresh for the analysis method that has been most recently applied to it. If it turns out that the sample is too old for a specific analysis method, the result obtained with such method has to be evaluated with particular care.

In another embodiment, the specific information is information on access rights to the sample. If a user has only temporarily limited access to a sample, such information can be used to no longer allow an analysis of the sample if an according analysis device is used that requires information on access rights to store or display any data or to perform a specific analysis.

In another embodiment, the specific information is information of previous analysis results obtained for the same sample. In doing so, results of different analyses can be retrieved and combined without the necessity of an external result data base.

Of course, it is possible that the specific information is a combination of any of the before-mentioned combinations. In addition, it is also possible to apply more than one marker to a sample in order to intrinsically encode different separated information.

In an embodiment, the analysis method is chosen from the group consisting of NMR spectroscopy, mass spectrometry, electron spin resonance, vibrational spectroscopy, UV/VIS spectroscopy, fluorescence spectroscopy and X-ray spectroscopy. NMR spectroscopy is particularly well suited as analysis method.

Whereas it is possible that the chemical marker is a single substance that can be, e.g., used in different concentrations to obtain a set of distinct markers, the chemical marker comprises in an embodiment at least two marking substances. In other embodiments, it might comprise at least three, in particular at least four, in particular at least five, in particular at least six, in particular at least seven, in particular at least eight, in particular at least nine and very particular at least ten marking substances. The more substances are used, the higher is the number of possible markers that can be built up from the according set of marking substances. Thereby, it is possible to combine a distinct number of different possible marking substances to a chemical marker. The mere presence of a marking substance in the chemical marker can then be indicative for distinguishing this chemical marker from another chemical marker in which a certain substance is not present or another marking substance is present instead. Thus, using different marking substances make it possible to rely on a qualitative analysis of the composition of the chemical marker in order to distinguish different chemical markers from each other.

In another embodiment, qualitative differences between the chemical markers are not the only criterion for distinguishing different chemical markers from each other. Rather, also quantitative aspects are considered in this embodiment. Therefore, in an embodiment, at least one marking substance is present in a defined concentration. If two or more, in particular three or more, in particular four or more, in particular five or more, in particular six or more, in particular seven or more, in particular eight or more, in particular nine or more and very particular ten or more marking substances are present in a defined concentration in the chemical marker, the concentrations of the marking substances are another unique identifier of the respective chemical marker. If, for example, six substances are used, wherein each substance can be used in 10 different concentrations, $10^6$ (1 million) different markers can be composed by this set of marking substances. Thus, one million different states are encodable by such a set of chemical markers.

Thus, it is possible to differentiate different chemical markers from each other only in quantitative aspects, i.e. with respect to the concentration of one or more marking substances being present in the chemical marker. In an embodiment, different chemical markers therefore comprise the same marking substances, wherein the defined concentration of at least one marking substance in a first chemical marker differs from the defined concentration of the same marking substance in a second chemical marker.

The chemical marker should be added to the sample in such a concentration that it can be reliably detected by the chosen analysis method. Thus, depending on the specific analysis method to be used for obtaining the marker-related result, different concentrations of the chemical marker might be required. In an embodiment, the chemical marker is added to the sample in a concentration of 0.1 to 1000 mmol/l, in particular 0.5 to 750 mmol/l, in particular 1 to 500 mmol/l, in particular 5 to 250 mmol/l, in particular 10 to 100 mmol/l, in particular 20 to 90 mmol/l, in particular 30 to 80 mmol/l, in particular 40 to 70 mmol/l, and very particular 50 to 70 mmol/l.

In an embodiment, the marking substance which forms part of the chemical marker is a saturated or unsaturated unsubstituted hydrocarbon like an alkane, alkene or alkyne. Cyclic hydrocarbons as well as aryls can also be used as marking substance. Such hydrocarbons are usually not soluble in water and not suited to be used in aqueous systems. However, they are very well suited to be used in all lipophilic solvents.

In another embodiment, the marking substance is a saturated or unsaturated hydrocarbon that is substituted and/or interrupted by one or more oxygen atoms, nitrogen atoms, phosphor atoms, metal atoms, halogen atoms, sulfur atoms and/or atoms of the fourth main group (carbon group) of the periodic table of elements.

In another embodiment, the marking substance is an alcohol. Alcohols have one or more hydroxyl groups covalently bound to an aliphatic carbon atom. Typical representatives are monovalent, primary, linear, non-branched alcohols like methanol, ethanol and propane-1-ol. Other typical representatives are monovalent, secondary and tertiary alcohols like isopropanol, butan-2-ol, and 2-methyl-propan-2-ol. Also very common are multivalent alcohols like ethylene glycol, propylene glycol and glycerol as well as unsaturated alcohols like allyl alcohol and crotonyl alcohol. Such alcohols are generally very well soluble in water if the carbon atom chain does not exceed six to eight carbon atoms and are thus well-suited for a use in aqueous samples to be analyzed.

In another embodiment, the marking substance is an aldehyde. Aldehydes comprise a terminal aldehyde group as functional group. Typical representatives are formaldehyde, acetaldehyde and propanal. Aldehydes are reactive and can therefore only be combined to a limited extent with other substances like amines.

In another embodiment, the marking substance is a carboxylic acid. Carboxylic acids bear one or more carboxyl groups as functional groups. Aliphatic, aromatic and heterocyclic carboxylic acids are suited as marking substance. Both saturated and unsaturated carboxylic acids can be used. Typical representatives are fatty acids (such as butyric acid, valeric acid and oleic acid) and acetic acid. Typical representatives of unsaturated acids are acrylic acid and linolenic acid. Also suited are dicarboxylic acids like oxalic acid and succinic acid as well as tricarboxylic acids like citric acid (an aliphatic tricarboxylic acid) and trimesic acid (an aromatic tricarboxylic acid). Further suited carboxylic acids are carboxylic acids that carry further functional groups like ketocarboxylic acids (like alpha-ketoglutaric acid), hydroxycarboxylic acids (like lactic acid and 3-hydroxypropionic acid) and amino acids (like alanine, glycine, phenylalanine, tryptophan and methionine or any other standard or non-standard naturally occurring amino acid). Further suited as marking substance are complex combinations of carboxylic groups in carbon matrices carrying other functional groups (like resin acids such as abietic acid and nicotinic acid belonging to the heterocyclic aromatic carboxylic acids).

In another embodiment, the marking substance is an ester. Esters can be obtained by the reaction of an acid and an alcohol under elimination of water. The acid can, e.g., be an organic acid like a carboxylic acid or a sulfonic acid or an inorganic acid like phosphoric acid, sulfuric acid, boric acid or carbonic acid. Typical representatives of esters are fats and oils (esters of glycerol and fatty acids), fruity esters, acetylsalicylic acid, sodium lauryl sulfate, nucleic acids and their components. The solubility of esters in water is diverse. Depending on the composition of the acid and the alcohol on the basis of which the esters are formed, the use of such esters as marking substances in aqueous samples is variably well possible.

In another embodiment, the marking substance is an ether. Ethers carry as functional group an ether group (an oxygen atom substituted by two organyl residues). Di-, oligo- and polysaccharides also formally belong to the group of ethers because their single units are connected with each other by a glycosidic bond being formed by an oxygen bridge between two carbon atoms. Such saccharides can also be referred to as acetals. Generally, linear, branched and cyclic ethers are known which are more or less water soluble. For example, the cyclic ethers tetrahydrofuran and 1,4-dioxane are unlimitedly miscible with water. Therefore, they are well suited as marking substances for aqueous samples.

In another embodiment, the marking substance is a ketone. Ketones carry a non-terminal carbonyl group as functional group. Low-molecular ketones are well water soluble due to the polarity of the carbonyl group. Ketones are less reactive than aldehydes and generally better suited than aldehydes as marking substances in aqueous samples.

All before-mentioned groups of chemical substances can also be subsumed under the term "organic oxygen compounds". In the following, organic nitrogen compounds will be explained in more detail.

In an embodiment, the marking substance is an amine. Generally, amines are derivatives of ammonia, wherein one or more hydrogen atoms are substituted by organic (e.g., alkyl or aryl) groups. They can generally be distinguished in primary, secondary, tertiary or quaternary ammonium compounds by their degree of substitution. All amines are generally detectable by nuclear magnetic resonance (NMR) so that they are well suited marking substances in case that NMR is used as analyzing method. Mono-, di- and trimethylamine or betaine are well suited examples of amines. Due to their polarity, amines are much better water-soluble that comparable hydrocarbons. It is possible that the substituents in secondary or tertiary amines are connected to a ring, like, e.g., in case of piperidine. Typical representatives of amines are amino acids or amino sulfonic acids (e.g. taurine).

In another embodiment, the marking substance is an amide. Amides are also derivatives of ammonia. Thereby, a hydrogen atom of ammonia is substituted by an acid residue. If organic acids are involved, the hydroxyl group of the acid is formally substituted by an —N—R1R2 group. R1 and R2 can hereby be either only hydrogen or also other residues. Suited amides are carboxamides which can form linear or cyclic structures. Examples of linear carboxamides are formamide, acetamide, N,N-dimethylformamide and urea. Examples of cyclic carboxamides are ε-caprolactam, phthalimide and penicillin. Other suited amides are peptides (amides between amino acids), polyamides, sulfonamides, phosphoramides or amides of other acids. The solubility behavior of such amides is dependent on the size and structure of the involved acids. Therefore, some amides are better suited than others for use in aqueous analysis systems or samples. Generally, amides are often soluble in water.

In another embodiment, the marking substance is a nitro compound. Nitro compounds can be divided in aliphatic and aromatic nitro compounds. Aliphatic nitro compounds are often reactive and occur frequently as synthetic intermediate products. Aromatic nitro compounds are generally more stable. Coloring agents like picric acid, Amido Yellow B and Pigment Green B are typical representatives of aromatic nitro compounds.

In another embodiment, the marking substance is a nitrile. Nitriles carry a nitrile or cyano group as functional group. Nitriles can be hydrolyzed and thus converted into carboxylic acids. If they shall be used in aqueous samples as marking substances, a detailed definition of the conditions under which such samples are handled is necessary. Otherwise, uncontrolled hydrolyzation of the nitriles might take place which would counterpart their general suitability as marking substance.

The chemical compounds explained in the following can be subsumed as sulfur compounds.

In an embodiment, the marking substance is an alkanethiol. Alkanethiols carry one or more aliphatically or aromatically bound thiol group as functional group. Typical representatives of alkanethiols are ethanethiol, dithiothreitol, glutathione, homocysteine, cysteine, coenzyme A, or penicillamine.

In another embodiment, the marking substance is a sulfide. Sulfides have the general structure R—S—R' and can be formed by alkyl and/or aryl residues. Sulfides are also referred to as thioethers. A typical representative of a sulfide is the amino acid methionine.

In another embodiment, the marking substance is a disulfide. Disulfides have the general structure R—S—S—R' and contain two sulfur atoms being bonded to each other. These sulfur atoms have a valance of 2. Typical examples of disulfides are dimethyl disulfide or diallyl disulfide.

In another embodiment, the marking substance is a sulfuric ester. Such sulfuric esters are sometimes also referred to as sulfates since their name often ends with "-sulfate". Examples of sulfuric esters are dimethyl sulfate or sodium lauryl sulfate.

In another embodiment, the marking substance is a sulfone. Sulfones have the general structure $R1—S(=O)_2—R2$. A simple example of a sulfone is dimethyl sulfone.

In another embodiment, the marking substance is a sulfoxide. Sulfoxides have the general structure $R1—S(=O)—R2$. A simple and quite common example of a sulfoxide is dimethyl sulfoxide (DMSO).

In another embodiment, the marking substance is a thionamide (such as chlorthiamide), a thiolester or a thioacid. Compounds belonging to these groups are generally well suited for marking aqueous systems or samples.

The chemical compounds and groups explained in the following relate to phosphorous compounds.

In an embodiment, the marking substance is a phosphate. Phosphates mainly occur as natural substance in the field of biochemical metabolic processes in the form of activated substances (e.g. ATP, glucose-6-phosphate, ribulose-1,5-bisphosphate, UDP, cyclic AMP). Phosphates are well water soluble and are thus well suited to be used as marking substances for aqueous samples. Since phosphates frequently occur in natural sample systems, their application in such systems makes only sense under certain, strict prerequisites.

In an embodiment, the marking substance is a phosphane. Phosphanes are compounds comprising a trivalent phosphorous atom or an according phosphorous chain to which hydrogen or organic substituents are bound. Organic phosphanes with short alkyl groups are liquid and very sensitive to air, sometimes also light sensitive. Therefore, their use as marking substances is only partly useful for specific sample systems.

In a further embodiment, the marking substance is an organometallic compound. Such compounds are characterized by an organic residue or an organic compound directly bound to a metal atom. In case of NMR spectroscopy as chosen analysis method, in particular compounds carrying non-magnetic metals are suited since such non-magnetic metals still allow a measurement in the applied strong magnetic field. If other analysis methods than NMR spectroscopy are chosen, also compounds with magnetic metals can be used.

In a further embodiment, the marking substance is a compound substituted by non-metals. Examples of such compounds are mono- or poly-halogenated compounds. Examples for such compounds are chloroacetic acid, bromoacetic acid or iodoacetic acid. The reactivity of such substituted hydrocarbon compounds is regularly higher than the reactivity of non-substituted variants. An interaction of such substituted compound with the sample or a modification of the sample by such substituted compounds has to be checked prior to the use of such non-metal substituted compounds depending on the specific nature of the sample to be supplemented by such a marking substance.

In a further embodiment, the marking substance is a heterocyclic compound. Such heterocycles are cyclic compounds with ring-forming atoms of at least two different chemical elements. Typical examples are heterocycles with nitrogen, oxygen or sulfur. Aromatic heterocycles are also referred to as heteroaromatic rings. The heterocycles form an extensive class of compounds. They can be grouped by type and number of heteroatoms and by ring size and degree of saturation of the cyclic system. For example, well suited compound classes are saturated 3- to 7-membered rings having nitrogen, oxygen or sulfur as hetero atom. Examples for such compounds are aziridine, oxirane, thiirane, azetidine, oxetane, thietane, pyrrolidine, tetrahydrofuran, tetrahydrothiophene, piperidine, tetrahydropyran, tetrahydrothiopyran, hexamethyleneimine, hexamethylene oxide and hexamethylensulfid. Also well suited as marking substances are unsaturated 3- to 7-membered rings having nitrogen, oxygen or sulfur as heteroatom. Examples therefore are azirine, oxirene, thiirene, azete, oxetiumion, thietiumion, pyrrole, furan, thiophene, pyridine, pyryliumion, thiopyryliumion, azatropilidene, oxacycloheptatriene and thiotropilidene.

Examples of polycyclic ring systems are pyrazole, imidazole, benzimidazole, imidazoline, indole, quinoline, isoquinoline, purine, pyrimidine, oxazole.

In addition, also other elements can be incorporated as heteroatoms in the ring. Thus, phosphabenzene and arsabenzene being homologues of pyridine are well suited as marking substances. In addition, also phosphole or arsole as homologues of pyrrole are well suited as marking substances.

Not only cyclic compounds carrying heteroatoms, but also linear compounds carrying heteroatoms can be used as marking substances. Particularly well suited are compounds carrying substituents of the fourth main group of the periodic table of elements. This fourth main group is also referred to as carbon group. Amongst silicon, germanium, tin and lead the elements silicon and germanium are particularly well suited as heteroatoms in according compounds.

In an embodiment, the marking substance is a silane. Single silanes are often used as reference substances for NMR analyzes. For example, tetramethylsilane (TMS), sodium trimethylsilylpropionate (TSP), 4,4-dimethyl-4-silapentane-1-sulfonic acid (DSS) and 4,4-dimethyl-4-silapentane-1-ammonium trifluoroacetate (DSA) are often used as such reference substances. However, they are regularly only used to calibrate an according NMR spectrum but not to encode any specific information. The solubility of such compounds in aqueous and organic systems is different so that this group of compounds offers high variability concerning the use in many different sample systems.

In an embodiment, the marking substance is a biochemical compound. Such biochemical compounds are generally well suited as marking substances, wherein it is to be considered that their use might be limited if their content in the sample to be analyzed is not negligible or if such biochemical compounds shall be analyzed in the sample itself. Thus, the suitability as marking substance strongly depends on the concrete nature of the sample to be analyzed. Typical representatives of biochemical compounds are alkaloids, i.e. natural occurring, chemical heterogeneous and usually alkaline, nitrogenous organic compounds of secondary metabolism with more than 10 000 actually assigned substances. Further suited biochemical compounds are amino acids, carbohydrates (sugars, starches, glycogen, fructanes, celluloses and di- and oligosaccharides), proteins, steroids, terpenes and vitamins.

In an embodiment, all modifications of the basic carbon skeleton can also be coupled with different functional groups. Thus, for example, aliphatic hydrocarbons (aliphatics), saturated acyclic hydrocarbons (alkanes) or unsaturated acyclic hydrocarbons (alkenes and alkynes) can be functionalized with the above-mentioned functional groups or hetero atoms. Likewise, cyclic hydrocarbons, aromatic hydrocarbons (aromates) can be used as simple or condensed aromates.

All of the above-mentioned compounds or groups of compounds constitute single embodiments for the marking substance to be used. They can be combined in any desired way to make up a new group of compounds being another embodiment of the marking substance.

It is obvious from the preceding explanations that the marking substance can be any unspecific substance. It is neither necessary nor intended that specific markers like certain antibodies are used as components of the chemical marker. By using unspecific marking substances, any standard analysis method can be used to analyze the composition of the marker and thus to decode the information encoded in the chemical marker. It is neither necessary nor intended that substance-specific analysis methods like antigen-antibody reactions or comparable methods are used to analyze the composition of the chemical marker. Specifically, if a set of samples is marked by different chemical markers, the chosen analysis method is, in an embodiment, suited to analyze all chemical markers used. In an embodiment, the individual components of the chemical marker are likewise suited to be analyzed by the chosen analysis method.

In an embodiment, a single analysis method is used to analyze all samples of a set of samples and likewise all chemical markers used to mark the samples of the set of samples. Thus, only a single analysis method is necessary to perform a sample analysis and at the same time a sample (or information) identification based on the data or information encoded by the chemical marker.

In an embodiment, the marking substance is enriched with respect to an isotope having a low natural abundance. The term "low natural abundance" is to be understood such that it refers to all isotopes that are not the most-prominent isotope of a specific element. E.g., $^{12}C$ is the most-prominent isotope of carbon. $^{13}C$ and $^{14}C$ are isotopes of low natural abundance. Thus, it is possible to use mixtures of different isotopes of the respective elements for building up the marking substance. Such isotopes can be naturally occurring or synthetically produced isotopes.

In an embodiment, the marking substance is enriched with respect to $^{2}H$, $^{3}H$, $^{13}C$, $^{14}C$, $^{15}N$, $^{29}Si$, $^{30}Si$, $^{32}P$, $^{33}P$ and/or $^{35}S$. The use of radioactive isotopes ($^{3}H$, $^{14}C$, $^{31}Si$, $^{32}Si$, $^{32}P$, $^{33}P$ and $^{35}S$) is generally possible, wherein isotopes having a long half-live are generally better suited since they make it easier that the composition of the marker is not altered within a relevant time period.

In an embodiment, the marker comprises a first marking substance having a first abundance of a set of isotopes and a second marking substance, which is chemically identical to the first marking substance but which has a second abundance of the set of isotopes differing from the first abundance. Thus, in this embodiment, two markers are chemically identical, but differ in the isotopic composition of the used marking substances. There exist many analysis methods which can differentiate between different isotopes. If an NMR spectroscopy is used as analysis method, signals of different isotopes can be made visible by a measurement in two different channels. In doing so, for example $^{12}C$ and $^{13}C$ can be analyzed at the same time. Thus, the isotopic ratios are directly available. Alternatively, the concentration of a $^{13}C$-marked substance can also be determined by using the satellite signals in a $^{1}H$ NMR spectrum. Summarizing, there are different possibilities to detect the composition of the marker, thus allowing to identify the marker and therewith the specific information encoded by this marker.

In another embodiment, the marker is already present in a sample tube prior to filling the sample into the sample tube. In doing so, the marker can, e.g., be present in the sample tube in liquid or solid form. It is particularly preferred if the marker is applied to the surface of the sample tube so that it is solved in the sample when the sample is filled into the sample tube. In other words expressed, the sample tubes can be pre-filled or pre-coated with a marker. This allows a particularly simple application of the instant method.

Already prior to filling the sample into an accordingly pre-marked tube, each individual tube can be distinguished from each other tube if a specific marker is only filled into a single tube. This distinction is even made easier after a sample has been added to the tube and after the sample has been analyzed as explained above. Thereby, the marker does not influence the chosen analysis method; it is only necessary that this method is suited to detect the marker. It is, however, also possible to perform more than one analysis method on a specific tube and thus a specific sample. One of these methods can be used to analyze the sample itself, wherein the other method can be used to analyze the chemical marker and thus serves to identify the sample. Generally, a single analysis method is more suited than a plurality of analysis methods to carry out the claimed method.

The invention relates also to a novel use of specific compounds for supplementing the sample with specific information that is not related to the compound itself. According suited compounds are chosen from the group consisting of saturated or unsaturated unsubstituted hydrocarbons, saturated or unsaturated hydrocarbons being substituted and/or interrupted by one or more oxygen atoms, nitrogen atoms, phosphor atoms, metal atoms, halogen atoms, sulfur atoms and/or atoms of the $4^{th}$ main group, alcohols, aldehydes, carbon acids, esters, ethers, ketones, amines, amides, nitro compounds, nitriles, alkane thiols, sulfides, disulfides, esters of sulfuric acid, sulfones, sulfoxides, thionamides, thiol esters, thioacids, phosphates, phosphanes, organometallic compounds, non-metal substituted compounds like halogen substituted compounds, heterocyclic compounds, silanes, alkaloids, amino acids, carbohydrates, proteins, steroids, terpenes and vitamins.

The invention relates also to a sample tube system comprising a plurality of sample tubes for receiving samples to be stored or analyzed, and a database. Such a sample tube system is characterized in that the sample tubes each comprise a chemical marker, wherein the chemical marker has a defined composition. In addition, the database contains data reflecting the composition of the chemical marker and information assigned to each chemical marker. This marker-assigned information is thereby not related to the composition of the chemical marker itself.

In an embodiment, each sample tube of the sample tube system might be equipped with a different chemical marker. This is in particular helpful if the individual samples shall be supplemented with a unique identifier. Alternatively, groups of sample tubes can be equipped with the same marker. This is particularly helpful if groups of samples shall be supplemented with the same specific information such as information on the origin of the sample if different samples originating from the same source are to be analyzed in different sample tubes.

In an embodiment, the chemical marker is deposited onto the inner surface of the respective sample tube. This deposition can, e.g., be carried out by coating the sample tube with the marker. For example, the marker can be coated in liquid form to the inner surface of the sample tube and then be dried or lyophilized. If then a liquid sample is applied to the sample tube, the marker is solved in the sample.

All specific embodiments explained with respect to the claimed method are also applicable to the claimed use and the claimed sample tube system in an analogous way, and vice versa.

BRIEF DESCRIPTION OF THE DRAWINGS

The invention will be explained in more detail with respect to an exemplary embodiment and a corresponding FIGURE.

FIG. 1 shows a schematic flow chart of an embodiment of a method for supplementing a sample with specific information.

DETAILED DESCRIPTION OF THE INVENTION

Please replace the paragraph on page 15, starting on line 4, to read as follows: In FIG. 1, a flow chart is depicted from which the general steps for supplementing a sample with specific information can be deduced. In a marking step 1, a previously obtained sample 2 is mixed with a marker 3. This marker comprises three marking substances A, B and C. In a storage step 4, data indicating the specific composition of the marker 3 and information assigned to this marker 3 is stored in a database 5. The information assigned to the marker 3 and to be stored in the database 5 in this example is "sample number 171". The storage step 4 can also be carried out prior to mixing the sample 2 with the marker 3.

In FIG. 1, a flow chart is depicted from which the general steps for supplementing a sample with specific information can be deduced. In a marking step 1, a previously obtained sample 2 is mixed with a marker 3. This marker comprises three marking substances A, B and C. In a storage step 4, data indicating the specific composition of the marker 3 and information assigned to this marker 3 is stored in a database 5. The information assigned to the marker 3 and to be stored in the database 5 in this example is "sample number 171". The storage step 4 can also be carried out prior to mixing the sample 2 with the marker 3.

Subsequently, the sample 2 containing the marker 3 is analyzed by NMR spectroscopy as analysis method in an analyzing step 6. NMR spectroscopy is suited to analyze the sample 2 and to detect a composition of the marker 3 in a qualitative and quantitative manner at the same time. Such, not only a sample-related result, but also a marker-related result is obtained. Subsequently, this marker-related result is compared in a comparing step 7 with the data stored in the database 5.

The marker-related result discloses the specific composition of the marker 3, namely the marking substances A, B and C and their concentration. In connection with the database 5, the marker-assigned specific information, namely "sample number 171" is thus decoded. Subsequently, this marker-assigned information can be assigned to the sample 2 in an according assignment step 8. Thus, it is clear that sample number 171 has been analyzed in analyzing step 6.

The invention claimed is:

1. A method for obtaining specific information on a sample, the method comprising the following steps:

adding a chemical marker having a defined composition to a sample,
storing data reflecting the composition of the chemical marker and information assigned to the chemical marker, wherein this marker-assigned information is not related to the composition of the chemical marker itself,
analyzing the sample with NMR spectroscopy so as to simultaneously obtain a) a sample-related result comprising data on the sample and b) a marker-related result comprising data on the marker composition,
comparing the marker-related result with the stored data,
assigning the marker-assigned stored information to the sample based on the preceding comparison,
obtaining the specific information assigned to the sample,
displaying and/or storing the sample-related result if the marker-assigned stored information matches predefined criteria, and
blocking the sample-related result if the marker-related result does not match predefined criteria.

2. The method according to claim 1, wherein the specific information is chosen from the group consisting of information for an unique identification of the sample, information on a user of the analysis method, information on a manufacturer of an ingredient of the sample, information on the origin of the sample, information on an expiration date of an ingredient of the sample, information on a term of a license, information on a time point at which the sample was obtained or manipulated, information on access rights to the sample, and information of previous analysis results obtained for the sample.

3. The method according to claim 1, wherein the chemical marker comprises at least two marking substances.

4. The method according to claim 3, wherein at least one marking substance is present in a defined concentration.

5. The method according to claim 3, wherein different chemical markers comprise the same marking substances, wherein the defined concentration of at least one marking substance in a first chemical marker differs from the defined concentration of the same marking substance in a second chemical marker.

6. The method according to claim 1, wherein the chemical marker is added to the sample in a concentration of 0.1 to 1000 mmol/l.

7. The method according to claim 1, wherein the chemical marker comprises a marking substance chosen from the group consisting of saturated or unsaturated unsubstituted hydrocarbons and saturated or unsaturated hydrocarbons being substituted and/or interrupted by one or more oxygen atoms, nitrogen atoms, phosphor atoms, metal atoms, halogen atoms, sulfur atoms and/or atoms of the $4^{th}$ main group.

8. The method according to claim 1, wherein the chemical marker comprises a marking substance chosen from the group consisting of alcohols, aldehydes, carbon acids, esters, ethers, ketones, amines, amides, nitro compounds, nitriles, alkane thiols, sulfides, disulfides, esters of sulfuric acid, sulfones, sulfoxides, thionamides, thiol esters, thioacids, phosphates, phosphanes, organometallic compounds, nonmetal substituted compounds like halogen substituted compounds, heterocyclic compounds, silanes, alkaloids, amino acids, carbohydrates, proteins, steroids, terpenes, vitamins.

9. The method according to claim 1, wherein the chemical marker comprises a marking substance which is enriched with respect to an isotope having a low natural abundance.

10. The method according to claim 9, wherein the marking substance is enriched with respect to $^2H$, $^3H$, $^{13}C$, $^{14}C$, $^{15}N$, $^{29}Si$, $^{30}Si$, $^{32}P$, $^{33}P$ and/or $^{35}S$.

11. The method according to claim 9, wherein the chemical marker comprises a first marking substance having a first abundance of a set of isotopes and a second marking substance being chemically identical to the first marking substance but having a second abundance of the set of isotopes differing from the first abundance.

* * * * *